United States Patent
Wassermann

(10) Patent No.: US 6,555,530 B1
(45) Date of Patent: Apr. 29, 2003

(54) USE OF ESTROGENS AND DELTA-GONADIEN-21-OL-3,20-DIONES FOR TREATING INSULIN DEPENDENT AND NON-INSULIN DEPENDENT DIABETES

(75) Inventor: Karsten Wassermann, Gentofte (DK)

(73) Assignee: Novo Nordisk A/S, Bagsvaerd (DK)

(*) Notice: Subject to any disclaimer, the term of this patent is extended or adjusted under 35 U.S.C. 154(b) by 0 days.

(21) Appl. No.: 09/494,700

(22) Filed: Jan. 31, 2000

Related U.S. Application Data

(63) Continuation of application No. PCT/DK00/00021, filed on Jan. 17, 2000.

(30) Foreign Application Priority Data

Jan. 18, 1999 (DK) .......................................... 1999 00051

(51) Int. Cl.[7] .......................... C07J 9/00; A61K 31/575; A61K 31/56
(52) U.S. Cl. .......................... 514/178; 552/548; 552/551; 552/553; 552/542; 552/541; 514/169
(58) Field of Search ................................. 552/541, 542, 552/548, 551, 553; 514/178, 170

(56) References Cited

U.S. PATENT DOCUMENTS 5,834,452 A * 11/1998 Biton et al. ................. 514/178
5,858,405 A * 1/1999 Gast ............................. 424/464

FOREIGN PATENT DOCUMENTS

WO  WO 98/04246   2/1998

OTHER PUBLICATIONS

Azner et al. (DN 84145330, CAPLUS, Contraception (1976), 13(3), 299–311).*
Abstract of Robinson et al., Diabetes Care, vol. 19, No. 5, pp. 480–485 (1996).
Abstract of Tchernof et al., Coron Artery Dis, vol. 9, No. 8, pp. 503–511 (1998).
Robinson et al., Diabetes Care, vol. 19, No. 5, pp. 480–485 (1996).
Tchernof et al., Coron Artery Dis, vol. 9, No. 8, pp. 503–511 (1998).

* cited by examiner

Primary Examiner—Sabiha Qazi
(74) Attorney, Agent, or Firm—Richard W. Bork, Esq.; Marc A. Began, Esq.; Reza Green, Esq.

(57) ABSTRACT

Analysis of full-blood glucose, serum insulin, serum triglycerides and total serum cholesterol were performed. Glucose levels in blood samples from the oral glucose tolerance test were used for calculation of the incremental Area Under the Curve ($AUC_{0\text{-}120\ min\text{-}baseline}$). All data are expressed as percentage change of vehicle treated animals (cf. FIGS. 1 and 2).

14 Claims, 2 Drawing Sheets

Figure 1:
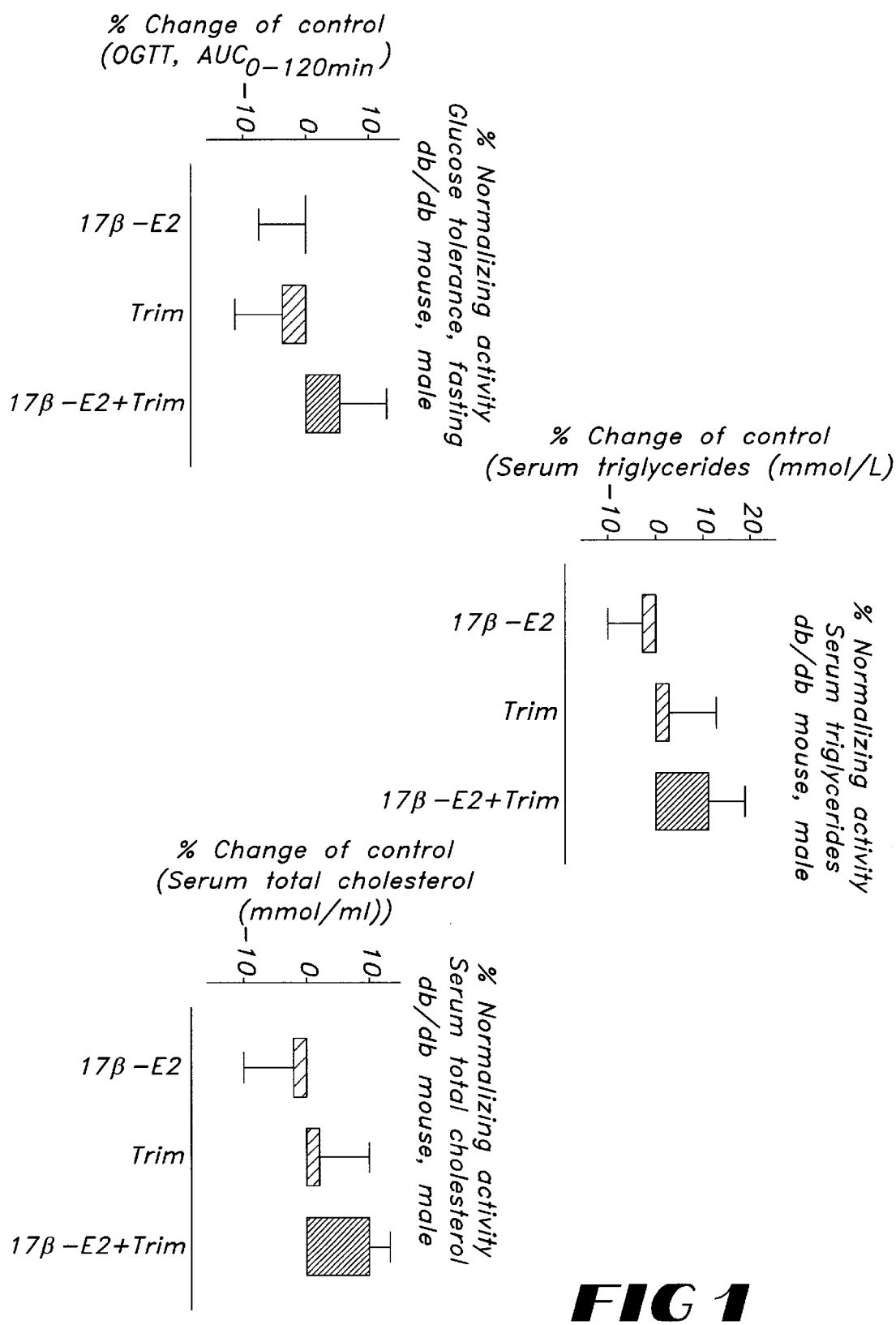
Figure 2:
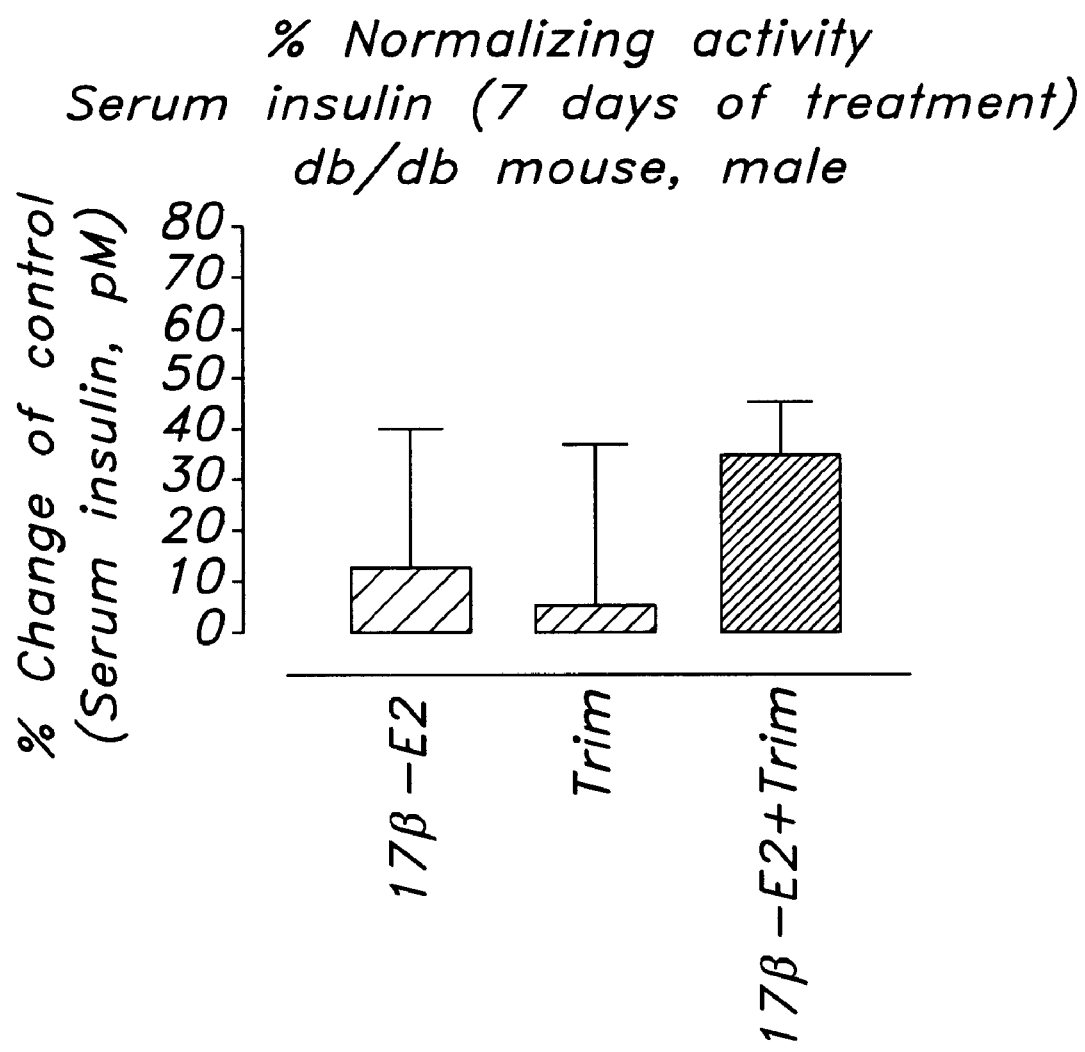

USE OF ESTROGENS AND DELTA-GONADIEN-21-OL-3,20-DIONES FOR TREATING INSULIN DEPENDENT AND NON-INSULIN DEPENDENT DIABETES

CROSS-REFERENCE TO RELATED APPLICATIONS

This application claims priority under 35 U.S.C. 119 of Danish application PA 1999 00051 filed on Jan. 18, 1999, and 35 is a continuation under U.S.C. 120 of PCT/DK00/00021 filed on Jan. 17, 2000, the contents of which are fully incorporated herein by reference.

FIELD OF THIS INVENTION

The present invention relates to the use of a combination of estrogens or SERMs with delta-gonadien-21-ol-3,20-diones for treating diabetes, particularly type II diabetes. The present invention also embraces pharmaceutical compositions and kits comprising these compounds and methods of using the compounds and their pharmaceutical compositions.

BACKGROUND OF THIS INVENTION

Diabetes mellitus is a systemic disease characterized by disorders in the actions of insulin and other regulatory hormones in the metabolism of carbohydrates, fats and proteins, and in the structure and function of blood vessels. The primary symptom of diabetes is hyperglycemia, often accompanied by glucosuria, the presence in urine of large amounts of glucose, and polyuria, the excretion of large volumes of urine. Additional symptoms arise in chronic or long standing diabetes. These symptoms include degeneration of the walls of blood vessels. Although many different organs are affected by these vascular changes, the nerves, eyes and kidneys appear to be the most susceptible. As such, long-standing diabetes mellitus, even when treated with insulin, is a leading cause of blindness.

There are two recognized types of diabetes. Type I diabetes is of juvenile onset, ketosisprone, develops early in life with much more severe symptoms and has a near-certain prospect of later vascular involvement. Control of this type of diabetes is difficult and requires exogenous insulin administration. Type II diabetes mellitus is of adult onset, ketosis-resistant, develops later in life, is milder and has a more gradual onset.

One of the most significant advancements in the history of medical science came in 1922 when Banting and Best demonstrated the therapeutic effects of insulin in diabetic dogs. However, even today, a clear picture of the basic biochemical defects of the disease is not known, and diabetes remains a serious health problem. It is believed that two percent of the United States' population is afflicted with some form of diabetes. The introduction of orally effective hypoglycemic agents was an important development in the treatment of hyperglycemia. Oral hypoglycemic agents are normally used in the treatment of adult onset diabetes.

Observations in animal models on glucose metabolism for type II diabetes and in humans suggest that sex steroids play a permissive role in the phenotypic expression of hyperglycemia. These observations have prompted studies on the effects of androgens and estrogens on blood glucose levels. Testosterone administration to intact or ovarectomized female rats resulted in marked insulin resistance which correlated to morphological changes in muscle, Holmang, et al., *Am.J.Physiol.*, 259, E555–560 (1990); Holmang, et al., *Am.J.Physiol.*, 262, E851–855 (1992). In streptozotocin diabetic rats, implanted testosterone antagonized the ability of residual insulin to maintain glycemic control, Le et al., *Endocrinology*, 116, 2450–2455 (1985). In contrast, glucosuria disappeared in castrated diabetic KK mice and reappeared when androgens were replaced in these mice, Nonaka, et al., *Jpn.J.Vet.Sci.*, 50, 1121–1123 (1988); Higuichi, et al., *Exp.Anim.*, 38, 25–29 (1989).

Results from estrogen administrations also support the hypothesis that the balance between androgens and estrogens is critical to the development of hyperglycemia. Daily estradiol administrations to diabetic KK mice normalized the blood glucose levels and eliminated glucosuria, Toshiro, et al., *Jpn.J.Vet.Sci.*, 51, 823–826 (1989). Estradiol also lowered the blood glucose levels of C57BL6J-ob/ob mice, Dubuc, *Proc.Soc.Exp.Biol.Med.*, 180, 468–473 (1985) and C57BL/KsJ-db/db mice, Garris, *Anatomical Record*, 225, 310–317 (1989).

In Biochemical and Biophysical Research Communications, (Dec. 24, 1996) 229 (3) 752–7, Diabetic Medicine, (September 1996) 13 (9 Suppl 6) s148-50 and Journal of Clinical endocrinology and metabolism, (September 1996) 81 (9) 3299–306, and several other journals, are disclosed insulin sensitizers, in particular thiazolidinediones, and their use in treating diabetes mellitus, in particular NIDDM. Insulin sensitizers lowers blood glucose without stimulating insulin secretion, and in some instances even lowers insulin levels in mammals.

There remains a need in the art for combined compositions and methods that are useful to reduce blood glucose concentrations. There is a further need for such compositions that lack or has decreased undesirable side effects of estrogen(s) and/or progesterone(s).

One object of the present invention is to provide compositions in one dosage form which can effectively be used to treat type II diabetes.

Another object of the present invention is to provide compositions, method of treatment or kits exhibiting a synergistic effect.

A further object of the present invention is to provide compositions, method of treatment or kits exhibiting no substantial side effects, such as high level of coronary heart disease events.

Other objects of the present invention will become apparent upon reading the present description.

DESCRIPTION OF THIS INVENTION

The present invention is based in part on the discovery that a representative combination of an estrogen or estrogen receptor modulator and a compound of formula I

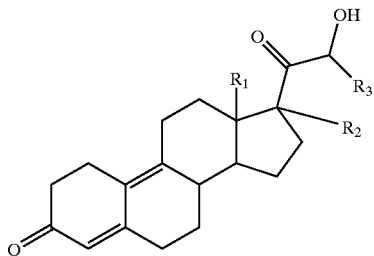

wherein $R_1$, $R_2$ and $R_3$ independently of each other are $C_{1-12}$alkyl, in the form of 21R or 21S epimers or mixtures thereof, or a pharmaceutically acceptable salt thereof, is effective for reducing blood glucose concentrations, and for treating type I and II diabetes in mammals, such as humans.

The present invention is based in part on the discovery that a representative combination of an estrogen or estrogen receptor modulator and a compound of formula I are also useful for treating conditions associated with insulin resistance. Conditions associated with insulin resistance can result from disorders such as diabetes mellitus and its chronic complications, obesity, hyperlipidemias and dyslipidemias, atherosclerosis, hypertension, cardiovascular disease, AIDS, cancer, wasting/cachexia, sepsis, trauma associated with burns, malnutrition and stress; aging, lupus and other autoimmune diseases, endocrine disease, hyperuricemia, polycystic ovary syndrome and complications arising from athletic activity or inactivity.

The combination of an estrogen or estrogen receptor modulator and a compound of formula I shows a synergistic effect in treatment of type I and II diabetes and/or in reducing blood glucose concentrations and/or a synergistic effect on side-effects, such as cardiovascular disorders, eg. lowering lipids.

In a first aspect the invention relates to a method of reducing blood glucose concentrations which method comprises administering to a subject an effective amount of an estrogen or estrogen receptor modulator in combination with an effective amount of a compound of formula I

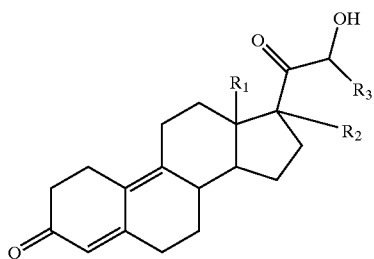

wherein $R_1$, $R_2$ and $R_3$ independently of each other are $C_{1-12}$alkyl, in the form of 21R or 21S epimers or mixtures thereof, or a pharmaceutically acceptable salt thereof, in an amount sufficient to reduce blood glucose concentrations.

In a second aspect the invention relates to a method of treating type I and II diabetes, preferably type II diabetes which method comprises administering to a subject an effective amount of an estrogen or estrogen receptor modulator in combination with an effective amount of a compound of formula I

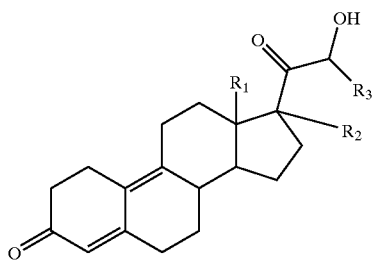

wherein $R_1$, $R_2$ and $R_3$ independently of each other are $C_{1-12}$alkyl, in the form of 21R or 21S epimers or mixtures thereof, or a pharmaceutically acceptable salt thereof, in an amount sufficient to treat type I and II diabetes, preferably type II diabetes.

In a third aspect the invention relates to a kit containing a treatment for type I and II diabetes, preferably type II diabetes comprising a) an effective amount of an estrogen or estrogen receptor modulator and a pharmaceutically acceptable carrier in a first unit dosage form; b) an effective amount of a compound of formula I

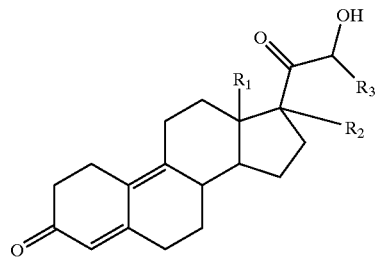

wherein $R_1$, $R_2$ and $R_3$ independently of each other are $C_{1-12}$alkyl, in the form of 21R or 21S epimers or mixtures thereof, or a pharmaceutically acceptable salt thereof, and a pharmaceutically acceptable carrier in a second unit dosage form; and c) container means for containing said first and second dosage forms.

In a fourth aspect the invention relates to a kit containing a treatment for reducing blood glucose concentrations comprising a) an effective amount of an estrogen or estrogen receptor modulator and a pharmaceutically acceptable carrier in a first unit dosage form; b) an effective amount of a compound of formula I

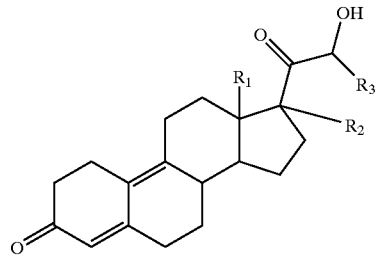

wherein $R_1$, $R_2$ and $R_3$ independently of each other are $C_{1-12}$alkyl, in the form of 21R or 21S epimers or mixtures thereof, or a pharmaceutically acceptable salt thereof, and a pharmaceutically acceptable carrier in a second unit dosage form; and c) container means for containing said first and second dosage forms.

In a further aspect the invention relates to a use of an estrogen or estrogen receptor modulator in combination with an effective amount of a compound of formula I

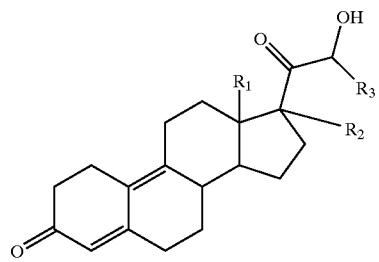

wherein $R_1$, $R_2$ and $R_3$ independently of each other are $C_{1-12}$alkyl, in the form of 21R or 21S epimers or mixtures thereof, or a pharmaceutically acceptable salt thereof, for the manufacture of a medicament for treating type I and II diabetes, preferably type II diabetes.

In a further aspect the invention relates to a use of an estrogen or estrogen receptor modulator in combination with an effective amount of a compound of formula I

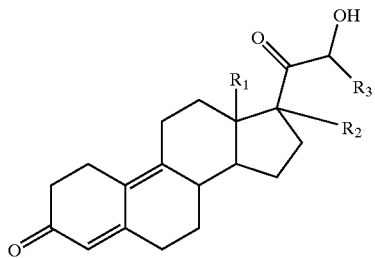

wherein $R_1$, $R_2$ and $R_3$ independently of each other are $C_{1-12}$alkyl, in the form of 21R or 21S epimers or mixtures thereof, or a pharmaceutically acceptable salt thereof, for the manufacture of a medicament for reducing blood glucose concentrations.

In a further aspect the invention relates to a composition, such as a pharmaceutical composition, comprising an estrogen or estrogen receptor modulator and a compound of formula I

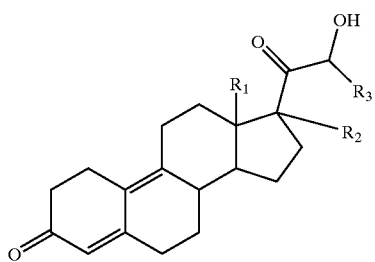

wherein $R_1$, $R_2$ and $R_3$ independently of each other are $C_{1-12}$alkyl, in the form of 21R or 21S epimers or mixtures thereof, or a pharmaceutically acceptable salt thereof, and a pharmaceutically acceptable carrier.

In one embodiment of the present invention the estrogen or estrogen receptor modulator and the compound of formula I is administered simultaneously in one dosage form, preferably orally as a tablet or capsule or as a transdermal patch.

In another embodiment of the present invention the estrogen or estrogen receptor modulator and the compound of formula I is administered substantially simultaneously.

In a further embodiment of the present invention $R_1$, $R_2$ and $R_3$ are independently of each other a $C_{1-6}$alkyl, such as $C_{1-4}$alkyl, preferably methyl.

In a further preferred embodiment of the present invention the compound of formula I is selected from

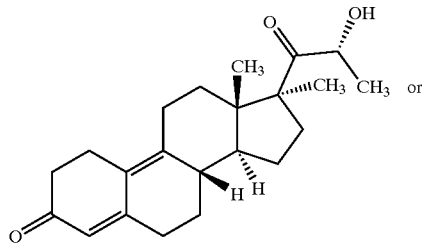

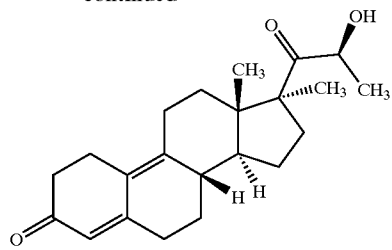

In a preferred embodiment of the present invention the compound of formula I is

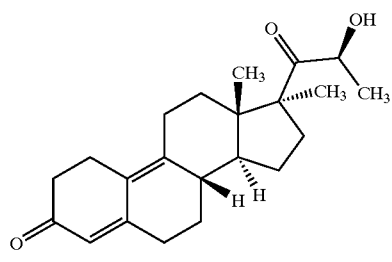

In a still further embodiment of the present invention the estrogen is selected from 17-beta-estradiol and esters thereof, ethinylestradiol, estriol (trihydroxyestrin), estrone, conjugated estrogens (eg. Premarin), sodium estrone sulfate, 8(9)-dehydroestradiol derivatives, 17alfa-dihydroequilin, equilenin, 17alfa-dihydroequilenin, esterified estrogens, and equilin, preferably 17-beta-estradiol and esters thereof, ethinylestradiol and conjugated estrogens. Each of these estrogens is individually considered an embodiment of the invention.

In a further embodiment of the present invention the estrogen receptor modulator is selected from droloxifene, raloxifene, tamoxifen, 4-hydroxy-tamoxifen, idoxifene, centchroman, levormeloxifene, Cis-6-(4-fluoro-phenyl)-5-[4-2-piperidin-1-yl-ethoxy)-phenyl]-5,6,7,8-tetrahydronaphthalene-2-ol; (−)-Cis-6-phenyl-5-[4-(2-pyrrolidin-1-yl-ethoxl)-phenyl]-5,6,7,8-tetrahydronaphthalene-2-ol; Cis-6-phenyl-5-[4-(2-pyrrolidin-1-yl-ethoxy)-phenyl]-5,6,7,8-tetrahydronaphthalene-2-ol; Cis-1-[6'-pyrrolidinoethoxy-3'-pyridyl]-2-phenyl-6-hydroxy-1,2,3,4-tetrahydronaphthalene;1-(4'-Pyrrolidinoethoxyphenyl)-2-(4'-fluorophenyl)-6-hydroxy-1,2,3,4-tetrahydroisoquinoline; Cis-6-(4-hydroxyphenyl)-5-[4-(2-piperidin-1-yl-ethoxy)-phenyl]-5,6,7,8-tetrahydronaphthalene-2-ol; and 1-(4'-Pyrrolidinoethoxyphenyl)-2-phenyl-6-hydroxy-1,2,3,4-tetrahydroisoquinoline. Each of these modulators is individually considered an embodiment of the invention.

In a still further embodiment of the present invention the effective amount of an estrogen or estrogen receptor modulator is from 0.00001 to 1000 mg/day, such as 0.01 to 2.5 mg/day and the effective amount of a compound of formula I is from 0.00001 to 1000 mg/day, such as 0.01 to 1.0 mg/day.

Within the present invention, the estrogen or estrogen receptor modulator and the compound of formula I may be prepared in the form of pharmaceutically acceptable salts, especially acid-addition salts, including salts of organic acids and mineral acids. Examples of such salts include salts of organic acids such as formic acid, fumaric acid, acetic acid, propionic acid, glycolic acid, lactic acid, pyruvic acid, oxalic acid, succinic acid, malic acid, tartaric acid, citric acid, benzoic acid, salicylic acid and the like. Suitable inorganic acid-addition salts include salts of hydrochloric, hydrobromic, sulphuric and phosphoric acids and the like. Each of these salts is individually considered an embodiment of the invention.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The $C_{1-12}$-alkyl, $C_{1-6}$-alkyl or $C_{1-4}$-alkyl groups specified above are intended to include those alkyl or alkylene groups of the designated length in either a linear or branched or cyclic configuration. Examples of linear alkyl are methyl, ethyl, propyl, butyl, pentyl, and hexyl and their corresponding divalent moieties, such as ethylene. Examples of branched alkyl are isopropyl, sec-butyl, tert-butyl, isopentyl, and isohexyl and their corresponding divalent moieties, such as isopropylene. Examples of cyclic alkyl are $C_{3-6}$- cycloalkyl such as cyclopropyl, cyclobutyl, cyclopentyl and cyclohexyl and their corresponding divalent moieties, such as cyclopropylene.

The compositions and kits of the present invention are useful within human and veterinary medicine, for example, in the treatment of patients suffering from type I and II diabetes, preferably type II diabetes. For use within the present invention, the estrogens or estrogen receptor modulators and compounds of formula I and their pharmaceutically acceptable salts are formulated with a pharmaceutically acceptable carrier to provide a medicament for parenteral, oral, nasal, rectal, subdermal or intradermal or transdermal administration according to conventional methods. Formulations may further include one or more diluents, fillers, emulsifiers, preservatives, buffers, excipients, etc. and may be provided in such forms as liquids, powders, emulsions, suppositories, liposomes, transdermal patches, controlled release, dermal implants, tablets, etc. One skilled in this art may formulate the compounds of formula I in an appropriate manner, and in accordance with accepted practices, such as those disclosed in *Remington's Pharmaceutical Sciences*, Gennaro, ed., Mack Publishing Co., Easton, Pa., 1990.

Oral administration is preferred. Thus, the estrogen or estrogen receptor modulator and compound of formula I are prepared in a form suitable for oral administration, such as a tablet or capsule, that is either a tablet or capsule containing both the estrogen or estrogen receptor modulator and compound of formula I in one dosage form, or a tablet or capsule containing the estrogen or estrogen receptor modulator in one dosage form and a tablet or capsule containing the compound of formula I in another dosage form. Typically, a pharmaceutically acceptable salt of the compound of formula I is combined with a carrier and moulded into a tablet. Suitable carriers in this regard include starch, sugars, dicalcium phosphate, calcium stearate, magnesium stearate and the like. Such compositions may further include one or more auxiliary substances, such as wetting agents, emulsifiers, preservatives, stabilizers, coloring additives, etc.

Pharmaceutical compositions containing the estrogen or estrogen receptor modulator and the compound of formula I may be administered one or more times per day or week. An effective amount of such a pharmaceutical composition is the amount that provides a clinically significant effect against type I and II diabetes, preferably type II diabetes. Such amounts will depend, in part, on the particular condition to be treated, age, weight, and general health of the patient, and other factors evident to those skilled in the art.

A typical oral dose will contain a nontoxic dosage range of from about 0.0001 to about 100 mg/kg patient per day of the estrogen or estrogen receptor modulator. A suitable oral dose of a compound of formula I is from 0.0001 to 100 mg/kg patient per day. In sequential regimen oral forms preferred dosages are from 0.001 to 50 mg, in particular 0.01 to 10 mg, more preferred 0.05 to 5 mg, most preferred 0.3 to 2.0 mg estrogen, eg. 17-beta-estradiol or conjugated equine estrogens, continuously combined with 10-14 days of 0.0001 to 10 mg, preferred 0.001 to 10 mg, in particular 0.01 to 5 mg, most preferred 0.05 to 0.5 mg of compound of formula I, eg. a compound of formula II. In continuous regimen oral forms preferred dosages are from 0.001 to 50 mg, in particular 0.01 to 10 mg, more preferred 0.05 to 5 mg, most preferred 0.3 to 2.0 mg estrogen, eg. 17-beta-estradiol or conjugated equine estrogens, continuously combined with 0.0001 to 10 mg, preferred 0.001 to 10 mg, in particular 0.01 to 5 mg, most preferred 0.05 to 0.5 mg of compound of formula I, eg. a compound of formula II, continuously.

A typical transdermal dose will contain a nontoxic dosage range of from about 0.00001 to about 100 mg/kg patient per day of the estrogen or estrogen receptor modulator. A suitable transdermal dose of a compound of formula I is from 0.00001 to 100 mg/kg patient per day. In sequential regimen transdermal forms preferred dosages are from 0.0001 to 50 mg, in particular 0.001 to 1 mg, more preferred 0.01 to 0.5 mg, most preferred 0.02 to 0.1 mg estrogen, eg. 17-beta-estradiol or conjugated equine estrogens, continuously combined with 10–14 days of 0.0001 to 10 mg, preferred 0.001 to 1 mg, in particular 0.01 to 0.5 mg, most preferred 0.05 to 0.4 mg of compound of formula I, eg. a compound of formula II. In continuous regimen transdermal forms preferred dosages are from 0.0001 to 50 mg, in particular 0.001 to 1 mg, more preferred 0.01 to 0.5 mg, most preferred 0.02 to 0.1 mg estrogen, eg. 17-beta-estradiol or conjugated equine estrogens, continuously combined with 0.0001 to 10 mg, preferred 0.001 to 1 mg, in particular 0.01 to 0.5 mg, most preferred 0.05 to 0.4 mg of compound of formula I, eg. a compound of formula II, continuously.

Subject or patient is intended to mean mammals, in particular humans, such as women in the menopause or postmenopausal women.

Treatment as used herein is intended to include profylactic treatment and palliative treatment.

The pharmaceutical compositions containing an estrogen or estrogen receptor modulator and a compound of formula I may be administered in unit dosage form one or more times per day or week. In the alternative, they may be provided as controlled release formulations suitable for dermal implantation. Implants are formulated to provide release of active compound over the desired period of time, which can be up to several years. Controlled-release formulations are disclosed by, for example, Sanders et al., *J.Pharm.Sci.* 73 (1964), 1294–1297, 1984. Controlled-release formulations are also disclosed by U.S. Pat. No. 4,489,056; and U.S. Pat. No 4,210,644, which are incorporated herein by reference.

Since the present invention relates to the prevention or treatment of type I and II diabetes, preferably type II diabetes by treatment with a combination of active ingredients which may be administered separately, the invention also relates to combining separate pharmaceutical compositions in kit form. The kit includes two separate pharmaceutical compositions: in one embodiment an estrogen and a delta4,9-gonadiene-21-ol-3,20-dione of formula I; and in another embodiment an estrogen receptor modulator and a delta4,9-gonadiene-21-ol-3,20-dione of formula I. The kit includes container means for containing the separate compositions such as a divided bottle or a divided foil packet. Typically the kit includes directions for the administration of the separate components. The kit form is particularly advantageous when the separate components are preferably administered in different dosage forms (e.g. oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relative of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

The term "estrogen" or "estrogens" has its conventional meaning and comprises estrogen and estrogen derivatives such as 17-beta-estradiol and esters thereof, ethinylestradiol, estriol (trihydroxyestrin), estrone, conjugated estrogens e.g. disclosed in U.S. Pat. Nos. 2,720,483 and 2,565,115, in particular premarin cf. internet place www.equinerescue.org/pmu_link.html, sodium estrone sulfate, 8(9)-dehydroestradiol derivatives as disclosed in WO 98/16544, 17alfa-dihydroequilin, equilenin, 17alfa-dihydroequilenin, esterified estrogens, and equilin.

Selective estrogen receptor modulators (SERMs), which previously were characterised as estrogen antagonists/partial agonists on their basis of their binding to the estrogen receptor alpha, act as full estrogen agonists in bone. The acronym SERM takes into account the fact that the activity of these agents is tissue selective and they cannot be definitely labeled as agonsists or antagonists but only as modulators of the estrogen receptor until their actions in specific tissues have been evaluated (Gustafsson, Current Opin Chem Biol 1998;2:508–511). Thus, the term "SERM"s or"estrogen receptor modulators" has its conventional meaning and comprises droloxifene, raloxifene, tamoxifen, 4-hydroxy-tamoxifen, idoxifene, centchroman, Cis-6-(4-fluoro-phenyl)-5-[4-2-piperidin-1-yl-ethoxy)-phenyl]-5,6,7,8-tetrahydronaphthalene-2-ol; (−)-Cis-6-phenyl-5-[4-(2-pyrrolidin-1-yl-ethoxy)-phenyl]-5,6,7,8-tetrahydronaphthalene -2-ol; Cis-6-phenyl-5-[4-(2-pyrrolidin-1 -yl-ethoxy)-phenyl]-5,6,7,8-tetrahydronaphthalene -2-ol; Cis-1-[6'-pyrrolidinoethoxy-3'-pyridyl]-2-phenyl-6-hydroxy-1,2,3,4-tetrahydronaphthalene; 1-(4'-Pyrrolidinoethoxyphenyl)-2-(4'-fluorophenyl)-6-hydroxy-1,2,3,4-tetrahydroisoquinoline; Cis-6-(4-hydroxyphenyl)-5-[4-(2-piperidin-1 -yl-ethoxy)-phenyl]-5,6,7,8-tetrahydronaphthalene-2-ol; 1-(4'-Pyrrolidinoethoxyphenyl)-2-phenyl-6-hydroxy-1,2,3,4-tetrahydroisoquinoline and the like.

The present invention is further illustrated by the following examples which, however, are not to be construed as limiting the scope of protection. The chemist of ordinary skill in the art will recognize that certain compounds related to this invention will contain one or more atoms which may be in a particular stereochemical or geometric configuration, giving rise to stereoisomers and configurational isomers. All such isomers and mixtures thereof are included within the present invention. Some of the compounds related to the present invention have assymetric carbon atoms and are enantiomers or diastereomers. Diastereomeric mixtures can be separated into their individual diastereomers on the basis of their physical chemical differences by methods known per se. Such methods may be chromatografy and/or fractional crystallization. Enantiomers can be separated by converting the enantiomeric mixture into a diastereomeric mixture by reaction with an appropriate optically active compound, eg. alcohol, separating the diastereomers and converting, eg. hydrolyzing, the individual diastereomers to the corresponding pure enantiomers. All such isomers, including diastereomers, enantiomers and mixtures thereof are considered a part of this invention.

The features disclosed in the foregoing description and in the following examples may, both separately and in any combination thereof, be material for realising the invention in diverse forms thereof.

EXAMPLES

Conjugated estrogens may be obtained following the process described in U.S. Pat. No. 2,720,483 or U.S. Pat. No. 2,565,115, which are incorporated herein by reference.

The compound having the formula II

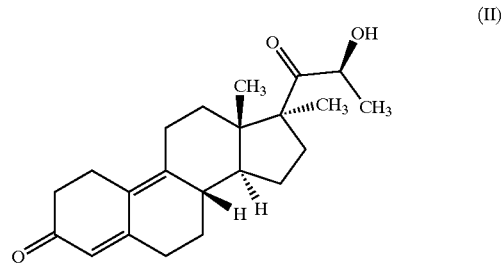

may be prepared as described in U.S. Pat. No. 4,273,771. The compound of formula II is called trimegestone.

An example of a tablet contains a conjugated estrogen (0,6 mg) and a compound of formula II (2,4 mg) formulated with pharmaceutically acceptable carriers to provide a medicament for oral administration according to conventional methods. The formulation further include the following diluents, fillers, emulsifiers, preservatives, buffers and/or excipients, that is calcium phosphate tribasic, calcium sulfate, canauba wax, cellulose, glyceryl monooleate, lactose, magnesium stearate, methylcellulose, pharmaceutical glaze, polyethylen glycol, sucrose, povidone, titanium dioxide and red ferric oxide. One skilled in this art may formulate the tablet composition in an appropriate manner, and in accordance with accepted practices, such as those disclosed in *Remington's Pharmaceutical Sciences*, Gennaro, ed., Mack Publishing Co., Easton, Pa., 1990.

Assessment of Pharmacological Activity in the
Type 2 Diabetic Mouse Model db/db

Animals

Male db/db mice were used as a model for type 2 diabetes. The db mouse is of C57BL/KsBom background and has the mutation localized to chromosome 4. The homozygotic db/db mouse is characterized by obesity, hyperphagia, hyperinsulinemia and hyperglycemia. As with most other conditions of hyperinsulinemia, the insulin response to glucose eventually becomes impaired leading ultimately to severe glucose intolerance Due to these phenotypic characteristics this mouse model is recognized as a model of type 2 diabetes. The animals used in these studies were 13 weeks of age and at a time point of hyperinsulinemia and severe hyperglycemia with modest hypertriglyceridemia. All animal procedures were conducted according to Novo Nordisk A/S Animal Care approved protocols, and the experiments were done in compliance with internal animal welfare and national guidelines.

The animals were allowed to adapt to the laboratory conditions for 2 weeks prior to the experimental procedure. Normal chow and tap water were freely available in the home cages throughout the studies. A normal 12 h/12 h light/dark regime was operative (lights on at 06.00 hours) and room temperature was held between 20–23° C.

Experimental Procedure

Animals were allocated to respective groups of treatment at the age of 13 weeks and with 6 animals per group. Full-blood glucose (non-fasting) was measured prior to treatment. Different groups of animals were injected SC daily with 17beta-estradiol valerate (0.03 mg/kg), trimegestone (0.30 mg/kg), a combination of 17beta-estradiol valerate (0.03 mg/kg) and trimegestone (0.30 mg/kg), or with the vehicle only (peanut oil). After 7 days of treatment full-blood glucose, serum insulin, serum triglycerides and total serum cholesterol were measured from samples of blood drawn from the retro-orbital sinus in non-fasting animals. An oral glucose tolerance test was performed on day 9 after an overnight fasting. Blood were sampled from the tail vein at time 0 min (baseline) and at 30, 60 and 120 min upon an oral glucose load of 3 g glucose/kg.

What is claimed is:

1. A method of treating type I or type II diabetes, said method comprising administering to a subject in need of such treatment:

(i) an effective amount of (a) an estrogen selected from the group consisting of 17-beta-estradiol and esters thereof, ethinylestradiol, estriol (trihydroxyestrin), estrone, conjugated estrogens, sodium estrone sulfate, 17alfa-dihydroequilin, equilenin, 17alfa-dihydroequilenin, esterified estrogens, and equilin, or (b) an estrogen receptor modulator selected from the group consisting of droloxifene, raloxifene, tamoxifen, 4-hydroxy-tamoxifen, idoxifene, centchroman, Cis-6-(4-fluoro-phenyl)-5-[4-2-piperidin-1-yl-ethoxy)-phenyl]-5,6,7,8-tetrahydronaphthalene-2-ol; (–)-Cis-6-phenyl-5-[4-(2-pyrrolidin-1-yl-ethoxy)-phenyl]-5,6,7,8-tetrahydronaphthalene-2-ol; Cis-6-phenyl-5-[4(2-pyrrolidin-1-yl-ethoxy)-phenyl]-5,6,7,8-tetrahydronaphthalene-2-ol; Cis-1-[6'-pyrrolidinoethoxy-3'-pyridyl]-2-phenyl-6-hydroxy-1,2,3,4-tetrahydronaphthalene; 1-(4'-Pyrrolidinoethoxyphenyl)-2-(4'-fluorophenyl)-6-hydroxy-1,2,3,4-tetrahydroisoquinoline; Cis-6-(4-hydroxyphenyl)-5-[4-(2-piperidin-1-yl-ethoxy)-phenyl]-5,6,7,8-tetrahydronaphthalene-2-ol; and 1-(4'-Pyrrolidinoethoxyphenyl)-2-phenyl-6-hydroxy-1,2,3,4-tetrahydroisoquinoline, in combination with:

(ii) an effective amount of a compound of formula I

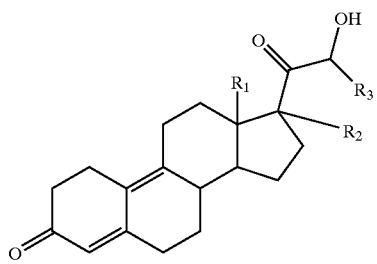

wherein $R_1$, $R_2$ and $R_3$ independently of each other are $C_{1-12}$ alkyl, in the form of 21R or 21S epimers or mixtures thereof, or a pharmaceutically acceptable salt thereof, wherein said first and second amounts in combination are effective to treat said type I or type II diabetes.

2. A method of reducing blood glucose concentrations, said method comprising administering to a subject in need of such treatment:

(i) an effective amount of (a) an estrogen selected from the group consisting of 17-beta-estradiol and esters thereof, ethinylestradiol, estriol (trihydroxyestrin), estrone, conjugated estrogens, sodium estrone sulfate, 17alfa-dihydroequilin, equilenin, 17alfa-dihydroequilenin, esterified estrogens, and equilin or (b) an estrogen receptor modulator selected from the group consisting of droloxifene, raloxifene, tamoxifen, 4-hydroxy-tamoxifen, idoxifene, centchroman, Cis-6-(4-fluoro-phenyl)-5-[4-2-piperidin-1-yl-ethoxy)-phenyl]-5,6,7,8-tetrahydronaphthalene-2-ol; (–)-Cis-6-phenyl-5-[4-(2-pyrrolidin-1-yl-ethoxy)-phenyl]-5,6,7,8-tetrahydronaphthalene-2-ol; (–)-Cis-6-phenyl-5-[4-(2-pyrrolidin-1-yl-ethoxy)-phenyl]-5,6,7,8-tetrahydronaphthalene-2-ol; Cis-1-[6'-pyrrolidinoethoxy-3'-pyridyl]-2-phenyl-6-hydroxy-1,2,3,4-tetrahydronaphthalene; 1-(4'-Pyrrolidinoethoxyphenyl)-2-(4'-fluorophenyl)-6-hydroxy-1,2,3,4-tetrahydroisoquinoline; Cis-6-(4-hydroxyphenyl)-5-[4-(2-piperidin-1-yl-ethoxy)-phenyl]-5,6,7,8-tetrahydronaphthalene-2-ol; and 1-(4'-Pyrrolidinoethoxyphenyl)-2-phenyl-6-hydroxy-1,2,3,4-tetrahydroisoquinoline, in combination with:

(ii) an effective amount of a compound of formula I

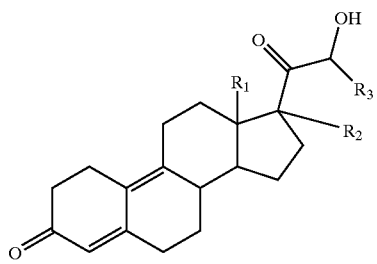

wherein $R_1$, $R_2$ and $R_3$ independently of each other are $C_{1-12}$ alkyl, in the form of 21R or 21S epimers or mixtures thereof, or a pharmaceutically acceptable salt thereof, wherein said effective amount of an estrogen or estrogen receptor modulator in combination with said effective amount of the compound of formula I are effective to reduce blood glucose concentrations.

3. A method according to claim 1 wherein the estrogen or estrogen receptor modulator and the compound of formula I are administered in one dosage form.

4. A method according to claim 1 wherein the estrogen or estrogen receptor modulator and the compound of formula I are administered simultaneously.

5. A method according to claim 1 wherein the compound of formula I is

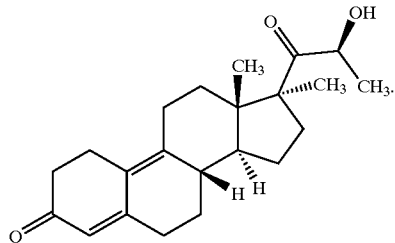

6. A method according to claim 1 wherein the effective amount of said estrogen or estrogen receptor modulator is from 0.0001 to 1000 mg/day and the effective amount of the compound of formula I is from 0.0001 to 1000 mg/day.

7. The method according to claim 1, wherein said effective amount in i) is of an estrogen selected from the group consisting of 17-beta-estradiol and esters thereof, ethinylestradiol, estriol (trihydroxyestrin), estrone, conjugated estrogens, sodium estrone sulfate, 17alfa-dihydroequilin, equilenin, 17alfa-dihydroequilenin, esterified estrogens, and equilin.

8. The method according to claim 7, wherein the estrogen is selected from the group consisting of 17-beta-estradiol and esters thereof, and conjugated estrogens.

9. The method according to claim 8, wherein the estrogen is selected from the group consisting of 17-beta-estradiol and esters thereof.

10. The method according to claim 7, wherein said compound of formula I is a compound of the formula:

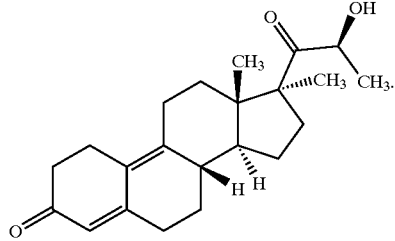

11. The method according to claim 8, wherein said compound of formula I is a compound of the formula:

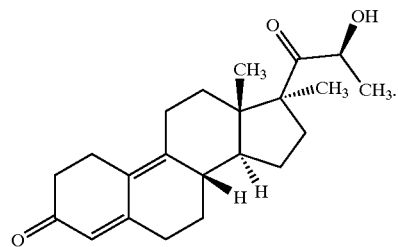

12. The method according to claim 9, wherein said compound of formula I is a compound of the formula:

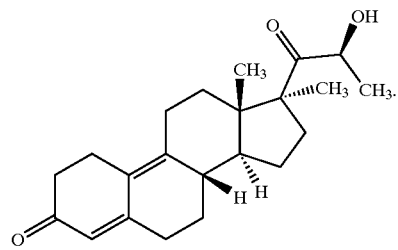

13. The method according to claim 1 wherein the effective amount in i) is of an estrogen receptor modulator selected from the group consisting of droloxifene, raloxifene, tamoxifen, 4-hydroxy-tamoxifen, idoxifene, centchroman, Cis-6-(4-fluoro-phenyl)-5-[4-2-piperidin-1-yl-ethoxy)-phenyl]-5,6,7,8-tetrahydronaphthalene-2-ol; (−)-Cis-6-phenyl-5-[4-(2-pyrrolidin-1-yl-ethoxy)-phenyl]-5,6,7,8-tetrahydronaphthalene-2-ol; Cis-6-phenyl-5-[4-(2-pyrrolidin-1-yl-ethoxy)-phenyl]-5,6,7,8-tetrahydronaphthalene-2-ol; Cis-1-[6'-pyrrolidinoethoxy-3'-pyridyl]-2-phenyl-6-hydroxy-1,2,3,4-tetrahydronaphthalene; 1-(4'-Pyrrolidinoethoxyphenyl)-2-(4'-fluorophenyl)-6-hydroxy-1,2,3,4-tetrahydroisoquinoline; Cis-6-(4-hydroxyphenyl)-5-[4-(2-piperidin-1-yl-ethoxy)-phenyl]-5,6,7,8-tetrahydronaphthalene-2-ol; and 1-(4'-Pyrrolidinoethoxyphenyl)-2-phenyl-6-hydroxy-1,2,3,4-tetrahydroisoquinoline.

14. The method according to claim 13, wherein the compound of formula I is a compound of the formula:

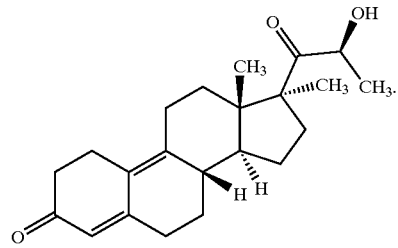

* * * * *